US012692214B2

(12) United States Patent
Ellwood et al.

(10) Patent No.: US 12,692,214 B2
(45) Date of Patent: Jul. 28, 2026

(54) PROCESS OF MAKING ORGANIC COMPOUNDS

(71) Applicant: Givaudan SA, Vernier (CH)

(72) Inventors: Simon Ellwood, Sissinghurst (GB); Chi-Lam Tse, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 533 days.

(21) Appl. No.: 18/268,918

(22) PCT Filed: Dec. 20, 2021

(86) PCT No.: PCT/EP2021/086720
§ 371 (c)(1),
(2) Date: Jun. 21, 2023

(87) PCT Pub. No.: WO2022/136232
PCT Pub. Date: Jun. 30, 2022

(65) Prior Publication Data

US 2024/0051904 A1 Feb. 15, 2024

(30) Foreign Application Priority Data

Dec. 22, 2020 (GB) ...................................... 2020330

(51) Int. Cl.
*C07C 29/147* (2006.01)

(52) U.S. Cl.
CPC .................................. *C07C 29/147* (2013.01)

(58) Field of Classification Search
CPC ....... C07C 29/147; C07C 67/36; C07C 33/02; C07C 69/587
See application file for complete search history.

(56) References Cited

U.S. PATENT DOCUMENTS

| | | | |
|---|---|---|---|
| 4,503,240 | A | 3/1985 | Staiger et al. |
| 2013/0273619 | A1 | 10/2013 | Bonnekessel et al. |

FOREIGN PATENT DOCUMENTS

| | | | |
|---|---|---|---|
| EP | 0107857 A1 | 5/1984 | |
| EP | 0553205 B1 | 4/1996 | |
| WO | 92/06063 A2 | 4/1992 | |
| WO | 2013/156398 A1 | 10/2013 | |
| WO | 2019237005 A1 | 12/2019 | |

OTHER PUBLICATIONS

Ohnuma S I, et al., "Undecaprenyl diphosphate synthase reaction with artificial substrate homologues—novel behavior in the termination of prenyl chain elongation", dated Jan. 1, 1989, pp. 6145-6160, vol. 45, No. 19, Tetrahedron, Elsevier Sience Publishers, Amsterdam, NL.
Ishihara, et al., "Enantio- and Diastereoselective Stepwise Cyclization of Polyprenoids Induced by Chiral and Achiral LBAs.A New Entry to (−)-Ambrox, (+)-Podocarpa-8,11, 13-triene Diterpenoids, and (−)-Tetracyclic Polyprenoid of Sedimentary Origin", dated Mar. 16, 2002, vol. 124, J. Am. Chem. Soc.
International Written Opinion for Application No. PCT/EP2021/086720 dated Apr. 26, 2022.
International Search Report for Application No. PCT/EP2021/086720 dated Apr. 26, 2022.

*Primary Examiner* — Deborah D Carr
(74) *Attorney, Agent, or Firm* — Curatolo Sidoti & Trillis Co., LPA; Floyd Trillis, III; Salvatore A. Sidoti

(57) ABSTRACT

There is provided a method for preparing homofarnesol (1), the method comprising the steps of:
a) providing farnesyl chloride (2)
b) reacting farnesyl chloride (2) to homofarnesate (3) by alkoxycarbonylation; and
c) reacting homofarnesate (3) to homofarnesol (1),
wherein the configuration of the double bonds in the compounds 1, 2 and 3 is preserved.

15 Claims, No Drawings

PROCESS OF MAKING ORGANIC COMPOUNDS

CROSS REFERENCE TO RELATED APPLICATIONS

This application is a national stage application of International Application No. PCT/EP2021/086720, filed 20 Dec. 2021, which claims priority from Great Britain Patent Application No. 2020330.3, filed 22 Dec. 2020, both of which applications are incorporated herein by reference.

The present invention relates to a new process for the preparation of homofarnesol, in particular (3E,7E)-homofarnesol. The invention is further concerned with the use of said homofarnesol as intermediate in the preparation of flavor and fragrance ingredients.

BACKGROUND

Homofarnesol is an important intermediate for the production of (−)-Ambrox (3a,6,6,9a-tetramethyldodecahydronaphtho[2,1-b]furan), a sought-after fragrance ingredient. The literature describes various processes for the preparation of homofarnesol. For example, it may be prepared by a lengthy process starting from Nerolidol (3,7,11-trimethyldodeca-1,6,10-trien-3-ol), via homofarnesylic acid amide (A. F. Barrero et al., J. Org. Chem. 1996, 61, 2215). Alternatively, homofarnesol may be prepared by carbonylation of Nerolidol in the presence of a polar solvent and a palladium halide catalyst (WO92/06063). Another way for the production of homofarnesol has been described by P. Kociensiki et al. (J. Org. Chem. 1989, 54, 1215), starting from dihydrofuran via five steps via homogeraniol. Also the synthesis of homofarnesol from geranylacetone via Wittig olefination, followed by cyclopropane ring opening and formyloxylation has been described in the literature (WO2013/156398). Those methods are relatively long and intensive in costs.

A useful intermediate for the preparation of homofarnesol is farnesyl chloride. Routes via this compound have not been studied in detail so far, in particular not with a focus on the double bond configuration.

It is therefore desirable to provide new or improved methods for making homofarnesol while controlling the double bond configuration.

SUMMARY

In accordance with a first aspect of the present invention there is provided a method for preparing homofarnesol (1)

(1)

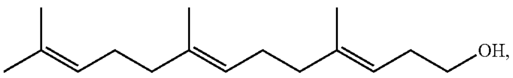

the method comprising the steps of:

a) providing farnesyl chloride (2)

(2)

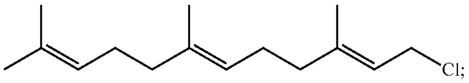

b) reacting farnesyl chloride (2) to homofarnesate (3) by alkoxycarbonylation (3)

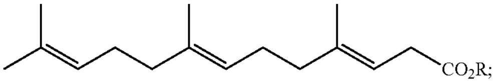

c) reacting homofarnesate (3) to homofarnesol (1);

wherein R is a $C_1$-$C_{10}$ alkyl group, for example Me, Et, n-propyl, i-propyl, n-butyl, i-butyl etc, including ring systems, optionally substituted; and wherein the configuration of the double bonds in the compounds 1, 2 and 3 is preserved.

Certain embodiments of any aspect of the present invention may provide one or more of the following advantages:

preservation of the double bond configuration;

efficient conversions;

mild reaction conditions;

simple and cost efficient reagents;

avoidance of difficult to handle waste;

avoidance of difficult work-up and purification; and avoidance of difficult to handle toxic reagents.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

The present invention is based on the surprising finding that homofarnesol (1) can be obtain from farnesyl chloride (2) under conditions allowing to preserve the configuration of the double bonds. Homofarnesol (1) is obtained without E/Z isomerization in good yields.

There is therefore provided herein a method for preparing homofarnesol (1)

(1)

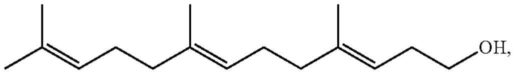

the method comprising the steps of:

a) providing farnesyl chloride (2)

(2)

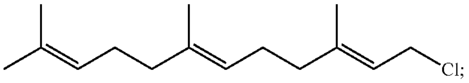

b) reacting farnesyl chloride (2) to homofarnesate (3) by alkoxycarbonylation (3)

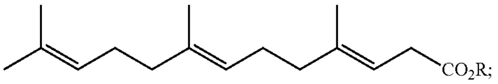

and c) reacting homofarnesate (3) to homofarnesol (1);

wherein R is a $C_1$-$C_{10}$ alkyl group, for example Me, Et, n-propyl, i-propyl, n-butyl, i-butyl etc, including ring systems, optionally substituted; and wherein the configuration of the double bonds in the compounds 1, 2 and 3 is preserved.

By this method homofarnesol (1) can be obtained in good yields without isomerization of the double bonds, in particular without isomerization of the C3 double bound which is close to the reaction site of the compound.

If no double bond configuration is indicated for a given compound, then the configuration is either not specified or refers to a mixture of isomers. For a certain configuration of a compound, the prefixes E- and Z- are used, for example (E,E)-1 or (3E,7E)-1.

If farnesyl chloride (2) is provided with a certain double bond configuration, said configuration will be maintained in the resulting homofarnesol (1). If farnesyl chloride (2) is provided as a mixture of double bond isomers, the resulting homofarnesol (1) will be obtained as a mixture of double bond isomers with a corresponding ratio. The described method is suitable to obtain homofarnesol (1) with a desired double bond configuration, as the configuration of the double bonds is preserved during the entire reaction sequence from the starting material to the final product. The method is suitable to provide homofarnesol (1) with any double bond configuration, in particular it is suitable to provide (3E,7E)-1. For the preparation of (3E,7E)-1, the starting material and the intermediate compounds possess also E,E configuration of the respective two double bonds, that is (E,E)-farnesyl chloride ((E,E)-2) and (E,E)-homofarnesate ((E,E)-3).

Farnesyl chloride (2) can be prepared for example in two steps from farnesene (4) via farnesyl amine (5), as described in WO 2019237005.

Step b) of the method for preparing homofarnesol (1), the reaction of farnesyl chloride (2) to homofarnesate (3), can be achieved by alkoxycarbonylation. The reaction is carried out in the presence of palladium on carbon as catalyst in aq. ethanolic solution under CO atmosphere. The double bond configuration of the substrate is preserved.

Step c) of the method for preparing homofarnesol (1), the reaction of homofarnesate (3) to homofarnesol (1), can be achieved by reduction with $NaAlH_2(OCH_2CH_2OCH_3)_2$ (CAS No. 22722-98-1, known under the trade names Red-Al or Vitride). Also, reduction with LAH is possible. Both organometallic reagents are used in stoichiometric or sub-stoichiometric amount. Alternatively, the conversion can be a hydrogenation in the presence of a homogenous catalyst. Also in this step, the double bond configuration of the substrate is preserved.

In one embodiment of the invention, there is provided a method for preparing homofarnesol (1) as described above, wherein the alkoxycarbonylation of farnesyl chloride (2) is carried out in the presence of a phase transfer catalyst. By the addition of a phase transfer catalyst, the formation of side products like ethers is lowered, and the alkoxycarbonylation rate is enhanced. Furthermore, the use of a phase transfer catalyst can reduce the amount of inorganic base, e.g. $K_2CO_3$ from 3 to 2 mol equivalents or lower, for example 1 mol equivalent or lower.

For example, the phase transfer catalyst can be selected from the group consisting of tetraalkylammonium salts, for example tetrabutylammonium halides as TBA-Cl, TBA-Br or TBA-I, or TBA-$HSO_4$.

In one embodiment of the reaction, the phase transfer catalyst is TBA-Br.

For example, the phase transfer catalyst is used in 1-10 mol % of farnesyl chloride (2), preferably in 3-8 mol %, more preferably 5 mol %.

In one embodiment of the invention, there is provided a method for preparing homofarnesol (1) as described above, wherein farnesyl chloride (2) is provided in a mixture with a carbamate (6)

(6)

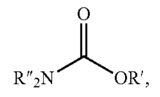

wherein R' is an alkyl group selected from Me, Et, n-Pr, optionally substituted, and the two R" residues are same or different alkyl groups selected from Me, Et, n-propyl, i-propyl, n-butyl, i-butyl etc, or the two R" residues form together a ring system, such as morpholine, pyrrolidine, which is optionally substituted.

Preferably, the two R" residues of the carbamate (6) are same alkyl groups selected from Et and n-propyl.

As mentioned above, farnesyl chloride (2) can be obtained in two steps from farnesene (4) via farnesyl amine (5). The amine is treated with an alkyl chloroformate $ClCO_2R'$, resulting in a mixture of farnesyl chloride (2) and the byproduct carbamate (6), wherein R' is an alkyl group selected from Me, Et, n-Pr, optionally substituted, and the two R" residues are same or different alkyl groups selected from Me, Et, n-propyl, i-propyl, n-butyl, i-butyl etc, or the two R" residues form together a ring system, such as morpholine, pyrrolidine, which is optionally substituted. Preferably, the two R" residues of the carbamate (6) are same alkyl groups selected from Et and n-propyl.

The carbamate (6) is usually removed before further conversion of farnesyl chloride (2) to avoid side reactions, for example by distillation. However, farnesyl chloride (2) is unstable; and as distillation is causing its partial decomposition, it is disadvantageous at this stage. Surprisingly, it was found, that the alkoxycarbonylation of farnesyl chloride (2) is possible in the presence of carbamate (6) without undesired side reactions. This allows the preparation of farnesyl chloride (2) with $ClCO_2R'$ from farnesyl amine (5), alkoxycarbonylation of the crude mixture without distillative removal of the carbamate (6) from the unstable farnesyl chloride (2), and easy separation of the more stable homofarnesate (3) from carbamate (6) by distillation.

So in one embodiment of the invention, there is provided a method for preparing homofarnesol (1) as described above, wherein farnesyl chloride (2) is provided as a mixture with carbamate (6), obtained from farnesyl amine (5) by treatment with an alkyl chloroformate $ClCO_2R'$.

In one embodiment of the reaction, there is provided a method for preparing homofarnesol (1) as described above, further comprising the preparation of farnesyl chloride (2) from β-farnesene (4)), by the following additional steps:

i) providing farnesene (4)

(4)

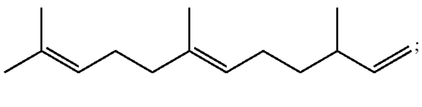;

ii) reacting farnesene (4) to farnesyl amine (5)

(5)

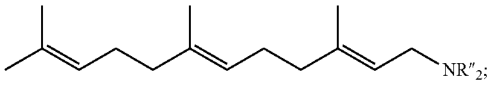

and iii) reacting farnesylamine (5) to farnesyl chloride (2)

(2)

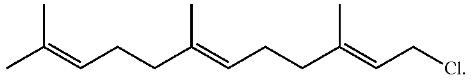

For the preparation of (E,E)-farnesyl chloride ((E,E)-2), the starting material is (E,β)-farnesene ((E,β)-4).

Step ii) in the method described above is a nucleophilic addition of a dialkylamine $R''_2NH$ to farnesene (4) in order to obtain farnesyl amine (5). The two R" residues are same or different alkyl groups selected from Me, Et, n-propyl, i-propyl, n-butyl, i-butyl etc, or the two R" residues form together a ring system, such as morpholine, pyrrolidine, which is optionally substituted. Preferably, the two R" residues are same alkyl groups selected from Et and n-propyl.

The dialkylamines $R''_2NH$ differ in boiling points and they can therefore affect the reaction conditions and handling. Their selection can also have an impact on the yield and E/Z ratio of the farnesyl amine (5). Best results are obtained with diethylamine and dipropylamine.

In one embodiment of the invention, the E/Z ratio of the double bond at C3 of homofarnesol (1) is greater than 80:20, more particularly greater than 85:15, still more particularly greater than 90:10.

In one embodiment of the invention, the E,E-homofarnesol ((E,E)-1) is present in 50 percent or more percent in the isomeric mixture, more particularly in 75 percent, more particularly in 85 percent or more, still more particularly in 90 percent or more.

In one embodiment of the invention, the alkoxycarbonylation reaction takes place under elevated pressure. For example, the reaction takes place under pressure of at least 2 bar or of at least 10 bar, or of at least 20 bar, or of at least 25 bar, or of at least 50 bar or more.

E,E-homofarnesol ((3E,7E)-4,8,12-Trimethyltrideca-3,7,11-trien-1-ol, (E,E)-1, disclosed for example in US2013/0273619A1 or by Kocienski et al, J. Org. Chem. 54(5), 1215-1217, 1989) is of particular interest, because the specific configuration provides, after cyclization under conditions known in the art, the very valuable fragrance ingredient known as Ambrox with a high content of the desired olfactorily active 3aR,5aS,9aS,9bR-enantiomer or the corresponding racemate (3aRS,5aSR,9aSR,9bRS) depending on reagents and conditions. For example, the cyclization can be carried out by biocatalytical means using Squalene Hopene Cyclase (SHC).

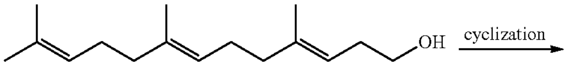

E,E-1

-continued

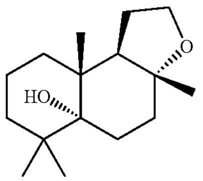

Ambrox

Therefore, in one embodiment of the invention, there is provided a method of preparing Ambrox, comprising the method for preparing (E,E)-homofarnesol ((E,E)-1) according to the methods described above, followed by cyclisation of (E,E)-homofarnesol ((E,E)-1)

((E,E)-1)

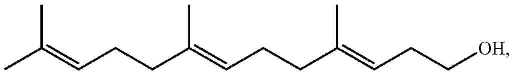

preferably by using the bacterial enzyme squalene hopene cyclase (SHC).

The invention is now further illustrated by the following non-limiting examples.

EXAMPLES

General:

GCMS: 50° C./2 min, 20° C./min 240° C., 35° C./min 270° C. Agilent 5975C MSD with HP 7890A Series GC system. Non-polar column: BPX5 from SGE, 5% phenyl 95% dimethylpolysiloxan 0.2 mm×0.25 μm×12 m. Carrier gas:helium. Injector temperature: 230° C. Split 1:50. Flow: 1.0 ml/min. Transfer line: 250° C. MS-quadrupol: 160° C. MS-source: 230° C. Injection vol. 1 μl. Ionization mode Electron Impact (EI) at 70 eV.

GC: 100° C./2 min, 15° C./min 240° C., 240° C./5 min. Thermo Focus GC. Non-polar column: Agilent Technologies J&W Scientific DB-5 ((5% Phenyl)-methylpolysiloxane) 0.32 mm×0.25 μm×30 m. Carrier gas:helium. FID-Detector, Detector temp. 270° C. Injector temperature: 240° C. Split 1:42.3. Pressure 70 kPa.

$^1$H- and $^{13}$C-NMR: Bruker-DPX-400 MHz spectrometer; spectra were recorded at 400 MHz ($^1$H) and 100 MHz ($^{13}$C) respectively in $CDCl_3$; δ in ppm rel. to $SiMe_4$; coupling constants J in Hz. The 3,4-EZ ratios of homofarnesol 1, farnesyl chloride 2, homofarnesate 3 and farnesyl amine 5 were determined by integration of the corresponding NMR peaks.

Abbreviations:

dppe bis(diphenylphosphino)ethane
Et ethyl
FC flash chromatography
GC gas chromatography
GCMS see GC and MS
Hz Hertz
M molecular weight
Me methyl
MS mass spectrometry, molecular sieve
MHz Megahertz
NMR nuclear magnetic resonance
Pr n-propyl
quant quantitative rpa general peak area (GC)

Ru-MACHO-BH Carbonylhydrido(tetrahydroborato)[bis (2-diphenylphosphinoethyl)-amino]ruthenium(II) (CAS 1295649-41-0)

TEBAB tetrabutylammonium bromide

Example 1: N,N'-Dipropyl E,E-farnesylamine (E,E)-5a

Dipropylamine (844 g, 8.34 mol), (E,β)-farnesene ((E,β)-4, 1 kg, 4.8 mol) and lithium (3.5 g, 0.5 mol) are heated for 2 h to 60° C. under nitrogen and stirring. The mixture is cooled to 25° C., and methanol (20 ml) is added to quench traces of remaining lithium. The mixture is filtered and the filter cake rinsed with methanol (220 ml). Methanol and dipropylamine are removed from the filtrate at 40° C./1 bar and the residue washed with water (1 l) and brine (300 ml). After drying over magnesium sulfate the crude product is distilled at 130° C./1 mbar giving 1245 g of N,N'-Dipropyl E,E-farnesylamine (E,E)-5a of 76% yield and 90% GC-purity.

$^1$H-NMR (400 MHz, $CDCl_3$): δ (ppm)=5.3 (m, 1H), 5.1-5.2 (2H), 3.1 (m, 2H), 2.35 (m, 4H), 1.9-2.2 (8H), 1.95-2.2 (8H), 1.65 (2 s, 6H), 1.55 (2 s, 6H), 1.73 (s, 3H), 1.65 (s, 3H), 1.6 (s, 6H), 1.4-1.5 (m, 4H), 0.85 (t, 6H).

$^{13}$C-NMR (100 MHz, $CDCl_3$): δ (ppm)=137.4 (s), 135.0 (s), 131.2 (s), 124.35 (d), 124.1 (d), 122.0 (d), 56.0 (t, 2C), 51.6 (t), 39.8 (t), 39.7 (t), 26.75 (t), 26.4 (t), 25.6 (q), 20.3 (t, 2C), 17.6 (q), 16.3 (q), 15.95 (q), 12.0 (q, 2C).

GCMS: m/z=305 $[M]^+$ (6%), 290 $[M-15]^+$ (3%), 276 (28%), 236 (58%), 168 (12%), 154 (100%), 137 (10%), 114 (21%), 100 (12%), 81 (41%), 72 (71%), 69 (67%), 55 (13%), 43 (18%), 41 (36%).

Comparative Example 2: Ethyl E,E-homofarnesate ((E,E)-3a) from E,E-farnesyl Chloride ((E,E)-2) Under Conditions of Kiji For the synthesis of E,E-farnesyl chloride see WO 2019237005 (Amyris).

Following general conditions described by Kiji et al (Chemistry Letters 1873-1876, 1989) a reaction flask with $Na_2PdCl_4$ (24 mg, 0.083 mmol, 0.65 mol %) and bis(diphenyl-phosphino)ethane (33 mg, 0.083 mmol) is evacuated and refilled 3 times with carbon monoxide. A solution of E,E-Farnesyl chloride ((E,E)-2, 3 g, 12.5 mmol, 2,3-EZ 98:2) in ethanol (5 ml) is added and the pink solution heated under 1 bar carbon monoxide to 50° C. At this temperature a mixture of sodium ethylate (4 g, 12.5 mmol) 21% in ethanol and ethanol (10 ml) are added dropwise within 2.5 h. After 1 h complete conversion is detected by GC and the reaction mixture cooled to 25° C. The carbon monoxide atmosphere is replaced by argon and the suspension poured onto water (50 ml), followed by extraction with methyl tert-butyl ether. The combined organic phase is washed with water and brine and is dried over $MgSO_4$. Filtration and evaporation of the solvents under reduced pressure gives 3.1 g of crude product which is purified by flash chromatography through silicagel giving farnesene (0.9 g), O-Ethyl nerolidol and E,E-farnesyl ethers (0.5 g), E,Z-homofarnesate (70 mg, 2% yield) and E,E-ethyl homofarnesate 3a (0.99 g, 28% yield) with an 3,4-EZ ratio of 93:7. The analytical data of the thus-obtained ethyl homofarnesate (E,E)-3a are identical to the ones obtained in a 3,4-EZ 76:24 mixture by C. Chapuis et al. in *Helv. Chim. Acta* 102 (7), 2019. This experiment shows that under the conditions of Kiji relatively low yield of Ethyl farnesate and byproducts are obtained.

Example 3: E,E-Ethyl Homofarnesate ((E,E)-3a) from E,E-farnesyl Chloride ((E,E)-2)

For the synthesis of E,E-farnesyl chloride see WO 2019237005 (Amyris).

An autoclave charged with E,E-Farnesyl chloride ((E,E)-2, 100 g, 332 mmol, 3,4-EZ ratio 90:10), potassium carbonate (143 g, 1.03 mol) and palladium on carbon (7.1 g, 3.3 mmol) in water (128 ml) and ethanol (300 ml) is stirred under 25 bar carbon monoxide for 24 h. After filtration of the reaction mass and removal of the ethanol under reduced pressure the two-phase mixture is extracted with methyl tert-butyl ether. The combined organic phase is washed with aqueous $NaHCO_3$ and brine, dried over $MgSO_4$ and filtered. Removal of the solvent under reduced pressure gives 92.5 g 3a (71% yield based on E,E-isomers) of crude ethyl homofarnesate with purity of 80% (EZ) and an 3,4-EZ ratio of 89:11. The analytical data of the product are within the frame of the slightly different 3,4-EZ-ratios identical to the ones obtained in example 2.

Example 4: E,E-Ethyl Homofarnesate ((E,E)-3a) from N,N-Dipropyl E,E-farnesyl Amine ((E,E)-5a) Via E,E-Farnesyl Chloride ((E,E)-2)

Methyl chloroformate (111 g, 1.17 mol) is added slowly over 3 h to N,N-Dipropyl-E,E-farnesylamine ((E,E)-5a, 351 g, 1.03 mol) maintaining a reaction temperature of <25° C. After another 30 min at 25° C. the mixture is transferred to a 5 l autoclave. Tetrabutylammonium bromide (17 g, 53 mmol), Pd 5% on carbon (22 g, 10 mmol), ethanol (1 l) and $K_2CO_3$ (430 g, 3 mol) in water (385 g) are added. The autoclave is sealed, purged with carbon monoxide and pressurized to 25 bar. After 24 h stirring at 25° C. the pressure is released. Ethanol (250 ml) and water (250 ml) are added and the reaction mixture is filtered over Celite, followed by evaporation of the ethanol at 40° C./100 mbar. After extraction with methyl tert-butyl ether the combined organic phase is washed with saturated $NaHCO_3$ and brine until pH=7, dried over $MgSO_4$ and filtered. The solvents are removed under reduced pressure. The crude product 3a is flash-distilled giving a product which is fractionally distilled at 137° C./1 mbar head temperature giving 176 g (49% yield) of Ethyl homofarnesate 3a with a 3,4-EZ ratio of 91:9.

The analytical data of the product 3a are within the frame of the slightly different 3,4-EZ-ratios identical to the ones obtained in example 2.

Example 5: E,E-Homofarnesol ((E,E)-1) from E,E-Ethyl Homofarnesate ((E,E)-3a) Through Vitride Reduction Ethyl E,E-Homofarnesate ((E,E)-3a, 645 g, 1.9 mol, 3,4-EZ>90:1) is added dropwise to Vitride 65% in toluene (769 g, 2.5 mol) at 65-75° C. under nitrogen and stirring. One hour after completed addition the reaction mass is cooled to ambient temperature and poured slowly onto 20% NaOH (1 ltr) under stirring. After 30 min stirring the phases are separated. The aqueous phase is washed with toluene. The combined organic phase is washed with water, brine, dried over $MgSO_4$ and filtered. The solvent is removed under reduced pressure giving 634 g of crude product, which is flash distilled and then fractionally distilled at 128° C./1 mbar giving 351 g (69% yield) of E,E-Homofarnesol 1 with 87% purity (GC rpa, based on the E,E-isomer) and a 3,4-EZ ratio of 92:8. The analytical data of E,E-Homofarnesol 1 are consistent with the ones in the literature, see for example P. Kocienski, S. Wadman *J. Org. Chem.* 54, 1215 (1989).

Example 6: E,E-Homofarnesol ((E,E)-1) from E,E-Ethyl Homofarnesate ((E,E)-3a) Through Homcat Hydrogenation Ethyl E,E-Homofarnesate ((E,E)-3a, 1 g, 3.6 mmol) and Ru-Macho-BH (10.5 mg, 0.018 mmol) in tetrahydrofuran (10 ml) are hydrogenated in an autoclave at 100° C. under 50 bar of hydrogen. After 18 h complete conversion to the homoallylic alcohol is detected by GC. The mixture is filtered through a silica gel pad and the THF is removed under reduced pressure giving 0.83 g (97% yield) of E,E-Homofarnesol 1 as clear yellow liquid and with an 3,4-EZ ratio of 98:2. The analytical data of E,E-Homofarnesol 1 are consistent with the ones of the same compound synthesized in example 5.

The invention claimed is:

1. A method for preparing homofarnesol (1)

(1)

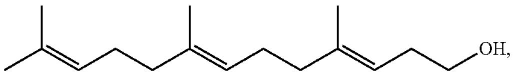

the method comprising the steps of:

a) providing farnesyl chloride (2)

(2)

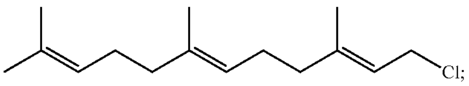

b) reacting farnesyl chloride (2) to homofarnesate (3) by alkoxycarbonylation in the presence of palladium on carbon as catalyst in aqueous alcohol under CO atmosphere (3)

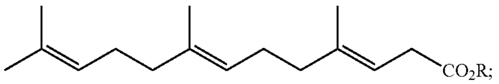

and c) reacting homofarnesate (3) to homofarnesol (1), wherein R is a $C_1$-$C_{10}$ alkyl group; and wherein the configuration of the double bonds in the compounds 1, 2 and 3 is preserved.

2. The method according to claim 1, wherein farnesyl chloride (2) is provided in a mixture with carbamate (6), (6)

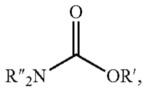

wherein R' is an alkyl group selected from Me, Et, n-Pr, and the two R" residues are same or different alkyl groups selected from Me, Et, n-propyl, i-propyl, n-butyl, i-butyl, or the two R" residues form together a ring system.

3. The method according to claim 2, wherein the two R" residues of carbamate (6) are the same alkyl groups selected from Et and n-propyl.

4. The method according to claim 1, wherein the E/Z ratio of the double bond at C3 of homofarnesol (1) is greater than 80:20.

5. The method according to claim 1, wherein R is Me or Et.

6. The method according to claim 1, wherein the reaction of homofarnesate (3) to homofarnesol (1) is a reduction.

7. The method according to claim 1, wherein the alkoxycarbonylation is carried out in the presence of a phase transfer catalyst.

8. The method according to claim 1, wherein R is selected from at least one of Me, Et, n-propyl, i-propyl, n-butyl, or i-butyl.

9. The method according to claim 1, wherein R includes one or more ring systems.

10. The method according to claim 1, wherein R is substituted.

11. The method according to claim 2, wherein R' is substituted.

12. The method according to claim 2, wherein the ring system comprises morpholine, pyrrolidine or combinations thereof.

13. The method according to claim 2, wherein the two R" residues are substituted.

14. The method according to claim 4, wherein the E/Z ratio of the double bond at C3 of homofarnesol (1) is greater than 85:15.

15. The method according to claim 4, wherein the E/Z ratio of the double bond at C3 of homofarnesol (1) is greater than 90:10.

* * * * *